United States Patent
Xu et al.

(10) Patent No.: US 9,650,332 B1
(45) Date of Patent: May 16, 2017

(54) PRODRUG OF PROBUCOL AND METHOD FOR PREPARING THE SAME

(71) Applicant: Yong Xu, San Diego, CA (US)

(72) Inventors: Yong Xu, San Diego, CA (US); Peter W Yohi, San Diego, CA (US); Michael Xu, San Diego, CA (US); Douglas Cruise, San Diego, CA (US)

( * ) Notice: Subject to any disclaimer, the term of this patent is extended or adjusted under 35 U.S.C. 154(b) by 0 days.

(21) Appl. No.: 15/184,817

(22) Filed: Jun. 16, 2016

(51) Int. Cl.
C07D 317/34 (2006.01)
C07C 321/26 (2006.01)
C07C 319/12 (2006.01)

(52) U.S. Cl.
CPC .......... *C07C 321/26* (2013.01); *C07C 319/12* (2013.01); *C07D 317/34* (2013.01)

(58) Field of Classification Search
None
See application file for complete search history.

(56) References Cited

U.S. PATENT DOCUMENTS 7,189,870 B2 * 3/2007 Somers ............... A61K 31/222
560/142

* cited by examiner

*Primary Examiner* — Timothy R Rozof
(74) *Attorney, Agent, or Firm* — Kile Park Reed & Houtteman LLC

(57) ABSTRACT

Provided is a compound of formula (II) as a prodrug of probucol, and a method for preparing the same, as well as a method for preventing or treating dyslipidemia with an effective amount of a compound of formula (II) to a subject in need thereof, (II)

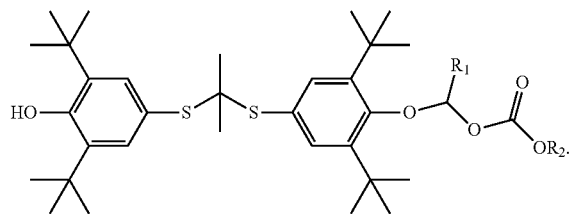

8 Claims, No Drawings

PRODRUG OF PROBUCOL AND METHOD FOR PREPARING THE SAME

FIELD

The present disclosure relates to a chemical medicine field, it relates generally to a prodrug of probucol, a method for preparing the same and a method for preventing or treating dyslipidemia.

BACKGROUND

Probucol is an anti-hyperlipidemic drug initially developed in the treatment of coronary artery disease. It has a formula (I) shown as below:

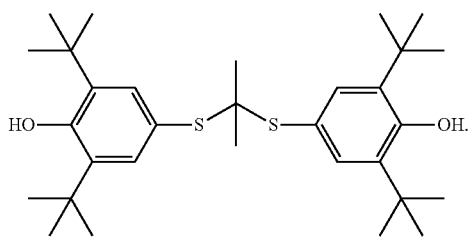

(I)

However, clinical trials were stopped after it was found that it may lower HDL in patients with a previous history of heart disease. Probucol was initially developed in the 1970s by a chemical company to maximize airplane tire longevity. Probucol is associated with QT interval prolongation. Due to the poor and irregularity of probucol's absorption from gastrointestinal tract, and some side effects like Q to T period extension in electrocardiogram and serious ventricular arrhythmia caused by probucol, adult patient usually take 0.5 g each time, and twice a day which makes the dose really large.

The current use of probucol still needs to be improved.

SUMMARY

It is an object of the present disclosure to provide the prodrug of probucol, thereby avoiding at least one of the disadvantages described above.

Prodrug, also known as drug precursor, is a compound that, after chemical structure modification, can be enzyme-metabolized from an inactive or less active condition into a pharmacologically active drug. The aim of this process is to improve the bioavailability of drug, enhance targeting, reduce drug toxicity and minimize side effects.

This invention is aimed to provide a prodrug of probucol. One approach is to remove a phenolic hydroxyl group and then introduce a hydrophilic segment in probucol. By using this method, the inactive prodrug can be metabolized into pharmacologically active ones that help cure some diseases, such as dyslipidemia, atherosclerosis, estenosis after angioplasty and xanthoma. The prodrug of probucol has a formula (II) shown as below:

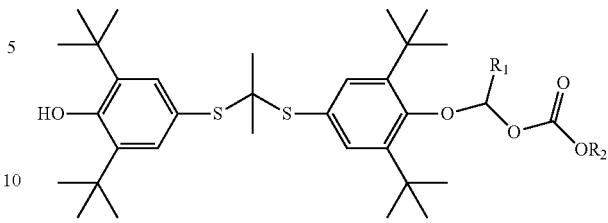

(II)

wherein $R_1$ is hydrogen or methyl, and $R_2$ is $C_1$-$C_6$ alkyl or cycloalkyl, optionally substituted by heteroatoms or heterocycles, In some embodiments, $R_2$ is selected from:

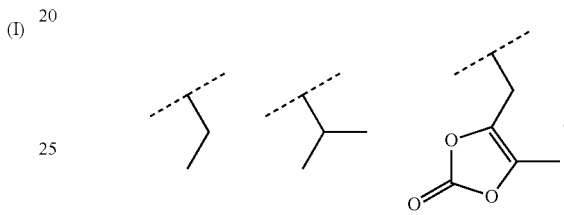

The compound of formula (II) in this invention can either be a racemate or a single optical isomer.

Another purpose for this invention is to provide a method for preparing a compound of formula (II), wherein the compound is synthesized by the scheme below:

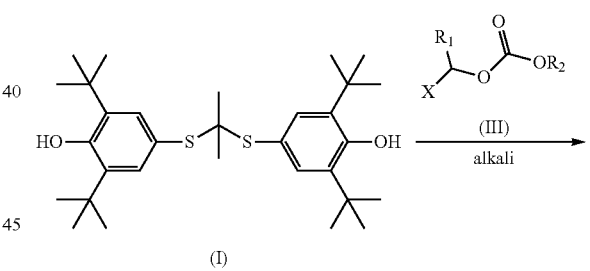

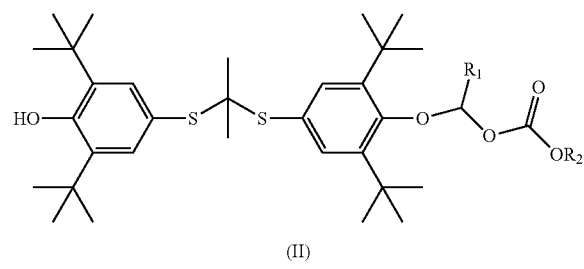

wherein $R_1$ is hydrogen or methyl, and $R_2$ is $C_1$-$C_6$ alkyl or cycloalkyl, optionally substituted by heteroatoms or heterocycles.

In some embodiments, $R_2$ is selected from:

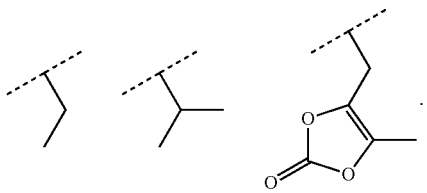

In some embodiments, the alkali is an inorganic base.

In some embodiments, the inorganic base is selected from a group consisting of sodium hydroxide, potassium hydroxide, sodium carbonate, potassium carbonate, cesium carbonate, sodium acetate and potassium acetate.

A further purpose of the present invention is to provide a method for preventing or treating dyslipidemia, including: administrating an effective amount of a compound of formula (II) to a subject in need thereof.

In addition, this invention directs to provide a targeted drug or compound that can help prevent and/or cure dyslipidemia. The drug or the composition contains the following characteristics: effective amount of the compound of formula (II) and at least one pharmaceutical acceptable carrier.

Through the animal experiments, it is demonstrated that the compound of formula (II) in this invention has good pharmacokinetic properties, the prodrug of probucol (the compound of formula (II)) can be transformed into probucol in vivo.

Compared with the prior art, the advantages of the present invention is as follows:

In the present invention, through the removal of one strong acidic phenolic hydroxyl group, the compound of formula (II) can increase the solubility of probucol, and improve the metabolic rate and meanwhile, minimize the side effects and adverse drug reactions.

DETAILED DESCRIPTION

The term "contacting" herein should be understood broadly, allowing any of at least two reactants react; for example, two reactants to be mixed under appropriate condition. According to the experimental requirements, mixing the reactants with which need to be contacted under stirring. Therefore, the type of agitation is not particularly limited. For example, may be a mechanical agitation, i.e. under the action of mechanical forces stirring.

As used herein, "a compound of formula N" is sometimes also referred to "Compound N". For example, "a compound of formula 2" may also be referred to "compound 2".

In this article, the term "first" or "second" is only used for describing objective other than indicate or imply relative importance or implicit indicate the number of technical features or technical solutions. Thus, defining the "first", the "second" features may explicitly or implicitly includes one or more of the characteristics. In the description of the disclosure, "multiple" means two or more, unless otherwise specifically limited.

According to the present disclosure, it is devised a prodrug of probucol as a compound of formula (II):

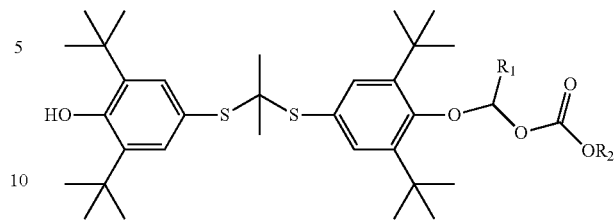

wherein $R_1$ is hydrogen or methyl, and $R_2$ is $C_1$-$C_6$ alkyl or cycloalkyl, optionally substituted by heteroatoms or heterocycles.

In some embodiments, $R_2$ is selected from:

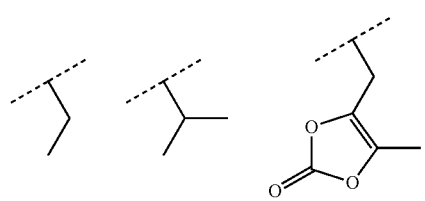

The compound of formula (II) in this invention can either be a racemate or a single optical isomer.

According to the present disclosure, another purpose for this invention is to provide a method for preparing a compound of formula (II), wherein the compound is synthesized by the scheme below,

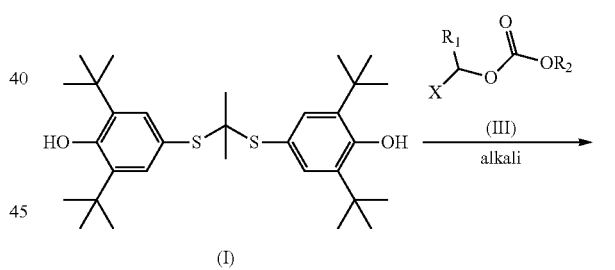

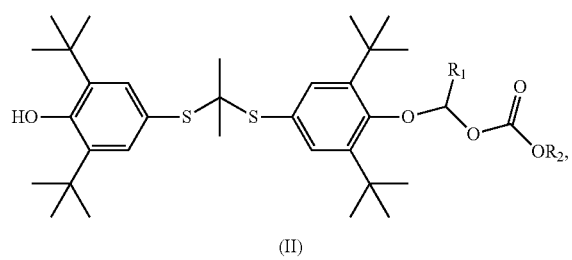

wherein $R_1$ is hydrogen or methyl, and $R_2$ is $C_1$-$C_6$ alkyl or cycloalkyl, optionally substituted by heteroatoms or heterocycles.

In some embodiments, R$_2$ is selected from:

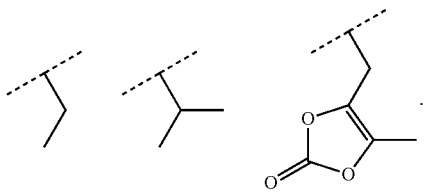

In some embodiments, the alkali is an inorganic base.

In some embodiments, the inorganic base is selected from a group consisting of sodium hydroxide, potassium hydroxide, sodium carbonate, potassium carbonate, cesium carbonate, sodium acetate and potassium acetate.

The technical solutions of the present disclosure include: the compound of formula (II) is prepared by a process including reacting the compound of formula (I) with the compound of formula (III).

In some embodiments, in the method disclosed herein, the preparation method of the present invention is as follows.

In a further aspect, there is provided a method for preventing or treating dyslipidemia, including: administrating an effective amount of a compound of formula (II) to a subject in need thereof.

In the present invention, the whole reaction route is simple, economic and easy to control, has high yield, and does not use harsh conditions such as high temperature and high pressure.

EXAMPLES

The preparation methods of formula (II) are disclosed in the examples of the present disclosure. Those skilled in the art can learn from this article to properly improve the process parameters to implement the preparation method. It's noted that all the similar replacements and changes are obvious for the skilled person and within the scope of the present disclosure. The methods disclosed herein are described in the preferred examples. Related persons can clearly realize and apply the techniques disclosed herein by making some changes, appropriate alterations or combinations to the methods without departing from spirit, principles and scope of the present disclosure.

In order to further understand the invention, it is detailed below through examples.

Example 1: Preparation of Compound (II-1)

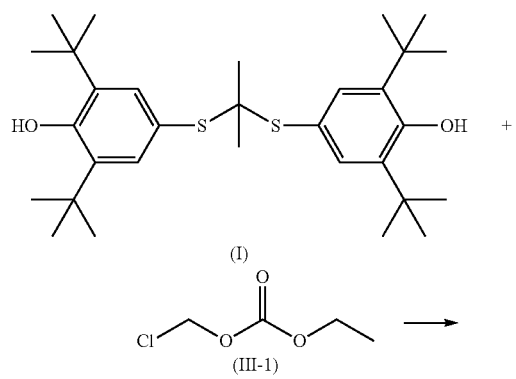

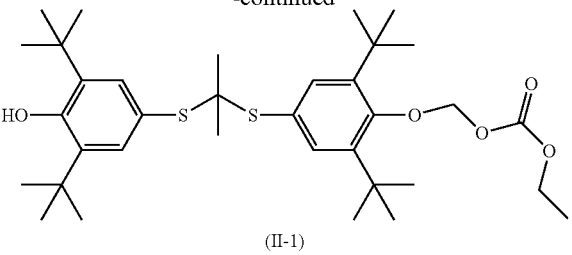

Probucol (520 mg, 1 mmol) was dissolved in 10 ml DMF. After adding 1 g sodium carbonate, the mixture was stirred under the chilled water condition, then adding compound (III-1) (145 mg, 1.15 mmol) and then being incubated with stirring at room temperature. 5 hours later, 30 ml distilled water was added to the mixture and the mixture was then extracted with ethyl acetate. The organic phase was separated, dried by anhydrous sodium sulfate and then being filtered. Rotary evaporators was used to treat the filtrate. The residue was purified by column chromatography and finally got compound (II-1) (386 mg, white solid).

$^1$H NMR (400 MHz, CDCl$_3$) δ 7.44 (s, 4H), 6.75 (s, 2H), 5.07 (s, 1H), 4.23 (q, J=8.4 Hz, 2H), 1.42 (s, 42H), 1.31 (t, J=8.3 Hz, 3H).

Example 2: Preparation of Compound (II-2)

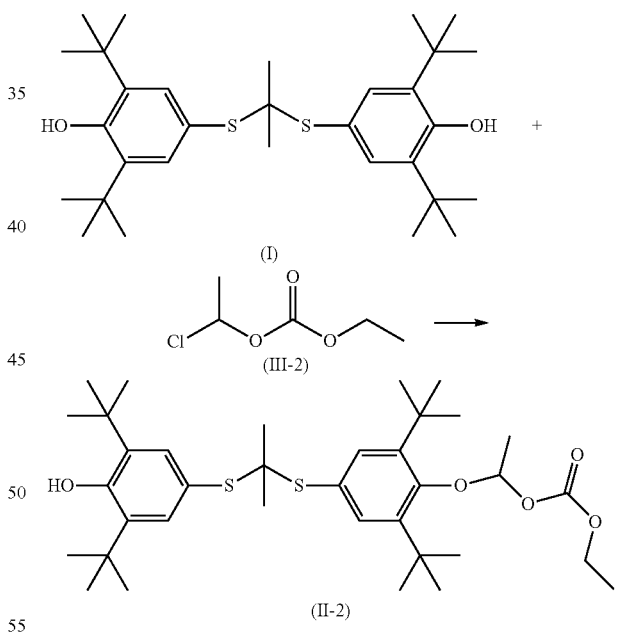

Probucol (520 mg, 1 mmol) was dissolved in 10 ml DMF. After adding 1 g sodium carbonate, the mixture was stirred under the chilled water condition, then adding compound (III-2) (175 mg, 1.15 mmol) and then being incubated with stirring at room temperature. 5 hours later, 30 ml distilled water was added to the mixture and the mixture was then extracted with ethyl acetate. The organic phase was separated, dried by anhydrous sodium sulfate and then being filtered. Rotary evaporators was used to treat the filtrate. The residue was purified by column chromatography and finally got compound (II-2) (392 mg, white solid).

$^1$H NMR (400 MHz, CDCl$_3$) δ 7.44 (s, 4H), 6.85 (m, 1H), 5.07 (s, 1H), 4.23 (q, J=8.4 Hz, 2H), 1.78 (d, J=6.4 Hz, 3H), 1.42 (s, 42H), 1.31 (d, J=8.3 Hz, 3H).

Example 3: Preparation of Compound (II-3)

Step 1: Preparation of Compound (III-3)

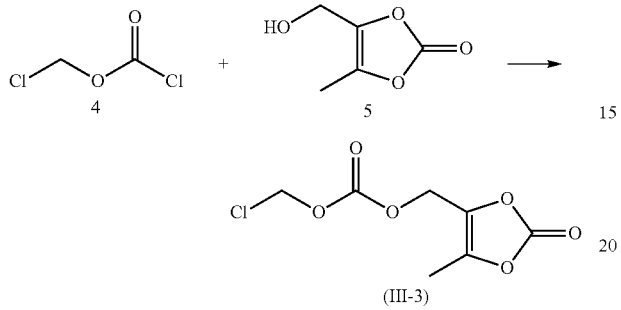

Compound 5 (2.6 g, 20 mmol) was dissolved in 10 ml dried dichloromethane. After adding 5 ml pyridine, the mixture was stirred under the cooling condition with the drops of Compound 4 (0.645 g, 5 mmol) and then being incubated overnight with stirring at room temperature. The next day, 30 ml saturated sodium bicarbonate was added to quench the reaction. The organic phase was separated, dried by anhydrous sodium sulfate and then being filtered. Rotary evaporators was used to treat the filtrate. The residue was purified by column chromatography and finally got compound (III-3) (0.924 g, light yellow liquid).

Step 2: Preparation of Compound (II-3)

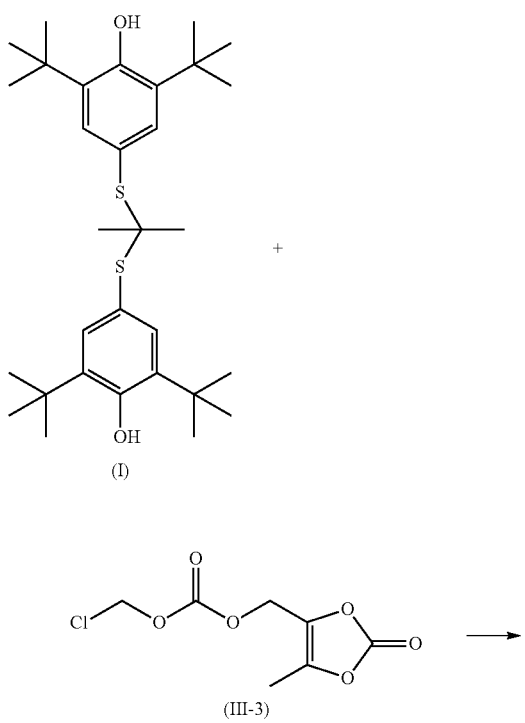

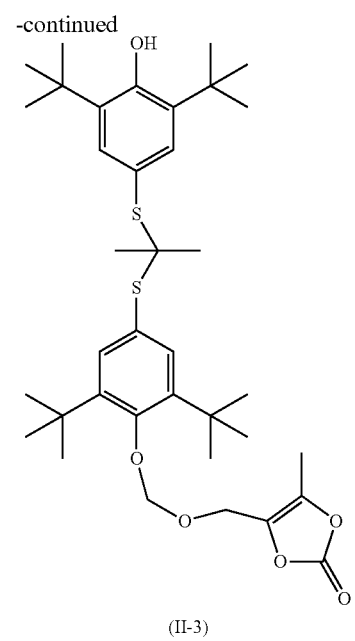

Probucol (520 mg, 1 mmol) was dissolved in 10 ml DMF. Under cooling condition, the mixture was added with compound (III-3) (255 mg, 1.15 mmol). After 5 hours stirring at room temperature, the mixture was extracted by ethyl acetate. The organic phase was dried by anhydrous sodium sulfate, and then being filtered. Rotary evaporators was used to treat the filtrate. The residue was purified by column chromatography and finally got compound (II-3) (325 mg, white solid).

$^1$H NMR (400 MHz, CDCl$_3$) δ 7.44 (s, 4H), 6.15 (s, 2H), 5.07 (s, 1H), 4.13 (s, 2H), 1.98 (s, 3H), 1.42 (s, 42H).

Example 4: Preparation of Compound (II-4)

Step 1: Preparation of Compound (III-4)

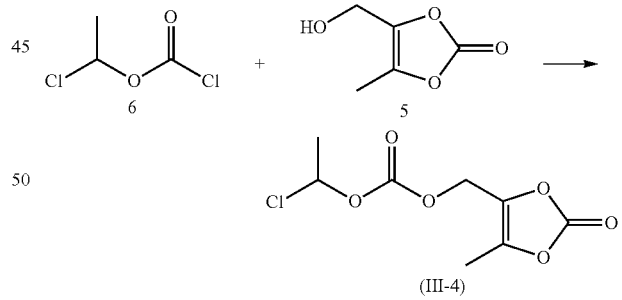

Compound 5 (2.6 g, 20 mmol) was dissolved in 10 ml dried dichloromethane. After adding 5 ml pyridine, the mixture was stirred under the cooling condition with the drops of Compound 6 (0.715 g, 5 mmol) and then being incubated overnight with stirring at room temperature. The next day, 30 ml saturated sodium bicarbonate was added to quench the reaction. The organic phase was separated, dried by anhydrous sodium sulfate and then being filtered. Rotary evaporators was used to treat the filtrate. The residue was purified by column chromatography and finally got compound (III-4) (0.804 g, light yellow liquid).

Step 2: Preparation of Compound (II-4)

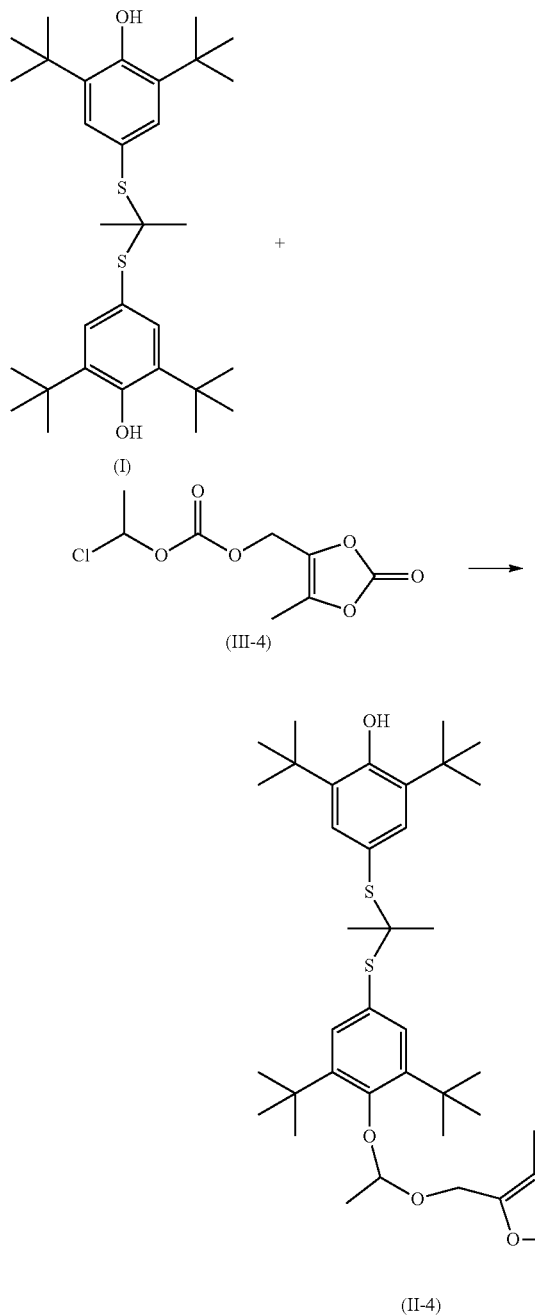

Probucol (520 mg, 1 mmol) was dissolved in 10 ml DMF. Under cooling condition, the mixture was added with compound (III-4) (271 mg, 1.15 mmol). After 5 hours stirring at room temperature, the mixture was extracted by ethyl acetate. The organic phase was dried by anhydrous sodium sulfate, and then being filtered. Rotary evaporators was used to treat the filtrate. The residue was purified by column chromatography and finally got compound (II-4) (334 mg, white solid).

$^1$H NMR (400 MHz, CDCl3) δ 7.44 (s, 4H), 6.18 (m, 1H), 5.07 (s, 1H), 4.13 (s, 2H), 1.98 (s, 3H), 1.59 (d, J=8.3 Hz, 3H), 1.42 (s, 42H).

Example 5: Biological Experiment: Pharmacokinetic Studies of the Prodrugs of Probucol in Rats

1. Objectives

Four different kinds of probucol's prodrugs were prepared based on the example 1, 2, 3 and 4 to evaluate their pharmacodynamic and pharmacokinetic characteristics in rats.

2. Protocol 2.1 Laboratory Animal Models:

Three Sprague Dawley Male Rats were used in each experiment for each prodrug. The laboratory animal models are provided by Shanghai Super-B&K laboratory animal Corp. Ltd. (No. Of animal license SYXK(HU)2008-0016).

2.2 Preparation of Investigational Drug

Weighed 20 mg sample and dissolved it with 1 ml ethanol. Then, in turn, added 1 ml Solutol HS15 and 8 ml pH4.63 acetate buffer to make the final solution with the concentration of 2 mg/ml. The left soup were saved to run quantitative analysis.

2.3 Dosing Administration

Three Sprague Dawley male rats were given the dose of 20 mg/mg (volume: 10 ml/kg) drugs by oral gavage under the condition of overnight fasting.

2.4 Sample Collection

Blood (volume: 0.1 ml) was drawn at 0.5, 1.0, 2.0, 4.0, 6.0, 8.0, 24.0 hours pre-dose and post-dose respectively to all animal subjects. Saved the blood samples in heparinized tubes and then centrifuged them for 10 minutes at 43500 rpm at 4° C. The separated plasma was stored at −20° C. All the process including blood collection and blood analysis should be conducted in low temperatures. Standard meals were provided after 2 hours of dosing.

3. Analytical Method 3.1 Instruments

API 4000 QTRAP LC/MS/MS (Applied Biosystems Corporation, US)

LC-20AD HPLC system (Shimadzu Corporation, Japan)

3.2 Chromatographic Conditions

| | |
|---|---|
| Chromatographic column | Inertsil C8-3 (50 × 4.6 mm, 5 μm) |
| Mobile phase | Acetonitrile: 0.5% formic acid(gradient elution) |
| Flow rate(ml/min) | 1.0 ml/min |

3.3 Condition of Mass Spectrometry

| | |
|---|---|
| Entrance Potential: | 10 psi |
| Collision Cell Exit Potential: | 12 psi |
| Curtain Gas: | 15 psi |
| Collision Gas: | Medium |
| Scan Mode: | ESI(+), MRM |
| IonSpray voltage | 5500 V |
| Temperature | 550° C. |
| Ion Source Gas 1 | 50 psi |
| Ion Source Gas 2 | 50 psi |
| MRM: | m/z 618.1 → 516.8 (example I), CE 29 eV, DP 95 V |
| | m/z 633.1 → 516.8 (example II), CE 26 eV, DP 70 V |
| | m/z 659.0 → 516.8 (example II), CE 29 eV, DP 62 V | m/z 674.0 → 516.8 (example IV),
CE 24 eV, DP 80 V
m/z 473.1 → 281.0 (YX1162, IS),
CE 33 eV, DP 127 V 3.4 Pretreatment of Plasma Samples The prodrug and metabolite probucol were measured at the same time. Took 25 ul rat plasma that drawn at different time points after dosing, and then added 50 ul internal standard YX1162 (200 ng/ml, prepared by acetonitrile) and 175 ul acetonitrile, vortex mixed for 3 minutes, and then centrifuged at 13500 rpm for 10 minutes. Took 10 ul supernatant to run LC/MS/MS analysis.

3.5 Standard Curve Preparation

The prodrug and metabolite probucol were measured at the same time. Took 25 ul rat blank plasma, then added 25 ul solution of standard series to make the drug concentration 1.00, 2.00, 5.00, 25.0, 100, 500, 2000, 20000 and 40000 ng/ml. Next, added 50 ul internal standard YX1162 (200 ng/ml, prepared by acetonitrile) and 150 ul acetonitrile, then followed the same protocol shown in 3.4.

Set plasma concentration as X-axis and the ratio of chromatographic peak areas for sample and internal standard as Y-axis, then used weighted least square method ($w=1/x^2$) to conduct linear regression analysis. The equations of standard curves were as shown in the figure:

| Sample name | The equation of standard curve | correlation coefficient (r) |
|---|---|---|
| Example I | y = 0.000870x + 0.00537 | 0.9994 |
| Example II | y = 0.00284x + 0.00359 | 0.9997 |
| Example III | y = 0.00195x + 0.00168 | 0.9978 |
| Example IV | y = 0.00413x + 0.0395 | 0.9948 |

4. Pharmacokinetic Studies of the Prodrug of Probucol in Rats 4.1 After rats were given 20 mg/kg prodrug of example 1, the concentration for the prodrug in blood indicated that the $t_{max}$ is (2.17±1.31) h, $C_{max}$ is (217.6±26.0) ng/ml, and $AUC_{0-t}$ is (758±204) ng/ml·h. Correspondingly, for metabolite probucol, the $t_{max}$ is (3.43±0.31) h, $C_{max}$ is (6544±2014) ng/ml, $AUC_{0-t}$ is (21045±2737) ng/ml·h, and $t_{1/2}$ 为 (10.03±0.04) h.

4.2 After rats were given 20 mg/kg prodrug of example 2, the concentration for the prodrug in blood indicated that the $t_{max}$ is (2.37±1.41) h, $C_{max}$ is (267.6±56.0) ng/ml, and $AUC_{0-t}$ is (1074±404) ng/ml·h. Correspondingly, for metabolite probucol, the $t_{max}$ is (2.75±0.49) h, $C_{max}$ is (3595±2101) ng/ml, $AUC_{0-t}$ is (23901±3404) ng/ml·h, and $t_{1/2}$ 为 (9.68±1.06) h.

4.3 After rats were given 20 mg/kg prodrug of example 3, the concentration for the prodrug in blood indicated that the $t_{max}$ is (2.57±1.01) h, $C_{max}$ is (367.6±78.0) ng/ml, and $AUC_{0-t}$ is (997±124) ng/ml·h. Correspondingly, for metabolite probucol, the $t_{max}$ is (2.50±0.47) h, $C_{max}$ is (16901±1142) ng/ml, $AUC_{0-t}$ is (48975±3365) ng/ml·h, and $t_{1/2}$ 为 (9.85±0.53) h.

4.4 After rats were given 20 mg/kg prodrug of example 4, the concentration for the prodrug in blood indicated that the $t_{max}$ is (3.31±1.31) h, $C_{max}$ is (597.6±75.0) ng/ml, and $AUC_{0-t}$ is (1067±174) ng/ml·h. Correspondingly, for metabolite probucol, the $t_{max}$ is (2.598±0.419) h, $C_{max}$ is (32538±1029) ng/ml, $AUC_{0-t}$ is (65776±3140) ng/ml·h, and $t_{1/2}$ 为 (10.54±2.07) h.

Conclusion: the four different prodrugs can all be metabolized into active pharmaceutical probucol in rats.

In the specification, unless specified or limited otherwise, terms such as "first" and "second" are used herein for purposes of description and are not intended to indicate or imply relative importance or significance.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound of formula (II) shown as below,

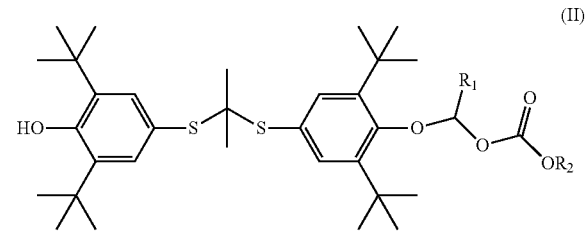

wherein $R_1$ is hydrogen or methyl, and $R_2$ is $C_1$-$C_6$ alkyl or cycloalkyl, optionally substituted by heteroatoms or heterocycles.

2. The compound according to claim 1, wherein $R_2$ is selected from:

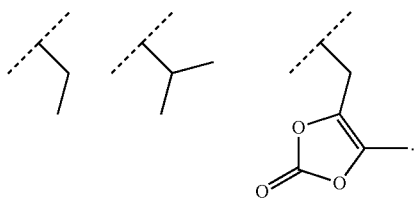

3. The compound according to claim 1, wherein the compound is a racemate or a single optical isomer.

4. A method for preparing a compound of formula (II), wherein the compound is synthesized by the scheme below,

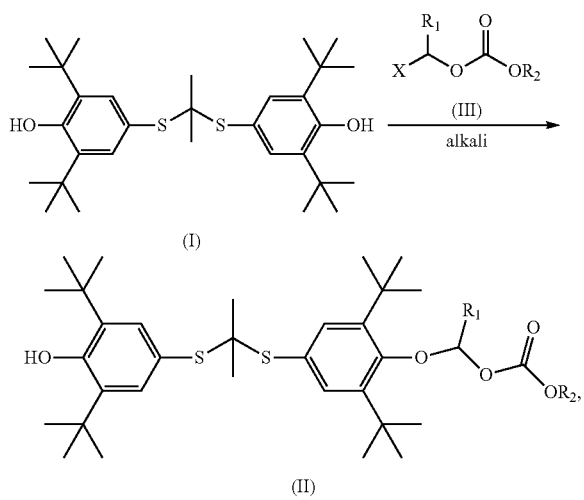

wherein $R_1$ is hydrogen or methyl, and
$R_2$ is $C_1$-$C_6$ alkyl or cycloalkyl, optionally substituted by heteroatoms or heterocycles.

5. The method according to claim 4, wherein $R_2$ is selected from:

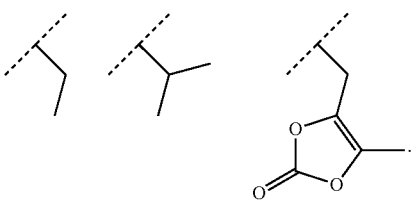

6. The method according to claim 4, wherein the alkali is an inorganic base.

7. The method according to claim 6, wherein the inorganic base is selected from a group consisting of sodium hydroxide, potassium hydroxide, sodium carbonate, potassium carbonate, cesium carbonate, sodium acetate and potassium acetate.

8. A method for treating dyslipidemia, comprising: administrating an effective amount of a compound of formula (II) to a subject in need thereof.

* * * * *